(12) United States Patent
Rao et al.

(10) Patent No.: US 8,642,758 B2
(45) Date of Patent: Feb. 4, 2014

(54) PROCESS FOR PREPARATION OF ERLOTINIB AND ITS PHARMACEUTICALLY ACCEPTABLE SALTS

(75) Inventors: Dharmaraj Ramachandra Rao, Maharashtra (IN); Rajendra Narayanrao Kankan, Maharashtra (IN)

(73) Assignee: Cipla Limited, Mumbai (IN)

( * ) Notice: Subject to any disclaimer, the term of this patent is extended or adjusted under 35 U.S.C. 154(b) by 373 days.

(21) Appl. No.: 12/593,212

(22) PCT Filed: Apr. 3, 2008

(86) PCT No.: PCT/GB2008/001186
§ 371 (c)(1),
(2), (4) Date: Dec. 7, 2009

(87) PCT Pub. No.: WO2008/122776
PCT Pub. Date: Oct. 16, 2008

(65) Prior Publication Data
US 2010/0094004 A1    Apr. 15, 2010

(30) Foreign Application Priority Data
Apr. 4, 2007    (IN) .......................... 681MUM/2007

(51) Int. Cl.
*C07D 239/94*    (2006.01)

(52) U.S. Cl.
USPC ....................................................... 544/293

(58) Field of Classification Search
USPC ....................................................... 544/293
See application file for complete search history.

(56) References Cited

FOREIGN PATENT DOCUMENTS

| EP | 0817775 B1 | 9/2001 |
|---|---|---|
| EP | 1044969 B1 | 12/2006 |
| IN | 902CHE2006 | 5/2006 |
| IN | 904CHE2006 | 5/2006 |
| WO | 9630347 A1 | 10/1996 |
| WO | 2004072049 A1 | 8/2004 |
| WO | 2008122776 A2 | 10/2008 |
| WO | 2008122776 A3 | 10/2008 |

OTHER PUBLICATIONS

Foreign communication from the priority application—International Search Report and Written Opinion, PCT/GB2008/001186, Jan. 26, 2009, 13 pages.

Knesl, Petr, et al., "Improved synthesis of substituted 6,7-Dihydroxy-4-quinazolineamines: tandutinib, erlotinib and gefitinib," Molecules, 2006, vol. 11, pp. 286-297.

Norris, Timothy, et al., "Discovery of a new stable polymorph of 4-(3-ethynylphenylamino)-6,7-bis(2-methoxyethoxy)quinazolinium methanesulfonate using near-infrared spectroscopy to monitor form change kinetics," J. Chem. Soc., Perkin Trans., 2000, vol. 2, pp. 2498-2502.

Foreign communication from the priority application—International Preliminary Report on Patentability, PCT/GB2008/001186, Oct. 6, 2009, 5 pages.

*Primary Examiner* — Brian McDowell
(74) *Attorney, Agent, or Firm* — Conley Rose, P.C.; Rodney B. Carroll

(57) ABSTRACT

A process for the preparation of a salt of N-(3-ethynylphenyl)-6,7-bis(2-methoxyethoxy)quinazolin-4-amine comprising reacting a 4-halo-6,7-bis(2-methoxyethoxy) quinazoline with 3-aminophenyl acetylene or an acid salt thereof under acidic conditions to form the corresponding acid salt of N-(3-ethynylphenyl)-6,7-bis(2-methoxyethoxy)quinazolin-4-amine, the process optionally further comprising converting the acid salt of N-(3-ethynylphenyl)-6,7-bis(2-methoxyethoxy)quinazolin-4-amine to N-(3-ethynylphenyl)-6,7-bis(2-methoxyethoxy)quinazolin-4-amine.

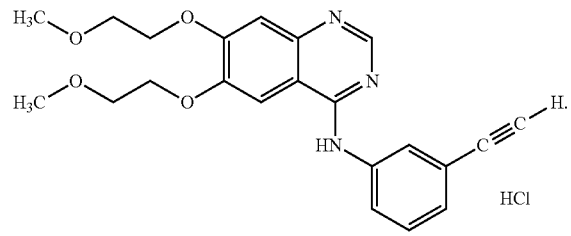

19 Claims, No Drawings

PROCESS FOR PREPARATION OF ERLOTINIB AND ITS PHARMACEUTICALLY ACCEPTABLE SALTS

CROSS-REFERENCE TO RELATED APPLICATIONS

This application is a filing under 35 U.S.C. 371 of International Application No. PCT/GB2008/001186 filed Apr. 3, 2008, entitled "Process for Preparation of Erlotinib and Its Pharmaceutically Acceptable Salts," claiming priority of Indian Patent Application No. 681/MUM/2007 filed Apr. 4, 2007, which applications are incorporated by reference herein in their entirety.

FIELD OF THE INVENTION

The present invention relates to an improved process for the synthesis of erlotinib and its pharmaceutically acceptable salts.

BACKGROUND OF THE INVENTION

Erlotinib is a Human Epidermal Growth Factor Receptor Type 1/Epidermal Growth Factor Receptor (HER1/EGFR) tyrosine kinase inhibitor.

Erlotinib is described chemically as N-(3-ethynylphenyl)-6,7-bis(2-methoxyethoxy)quinazolin-4-amine, and its hydrochloride salt is represented by the compound of Formula I.

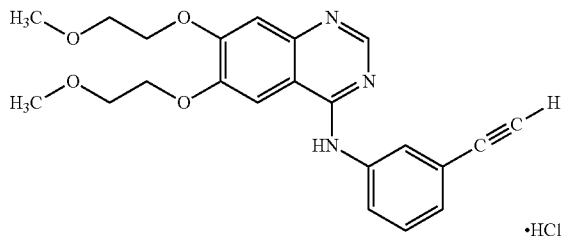

Erlotinib is disclosed in EP0817775 which also a discloses process for its preparation, which involves adding 3-ethynylaniline and 4-chloro-6,7-bis(2-methoxyethoxy)quinazoline in isopropanol containing pyridine and then refluxing the mixture for 4 hours under the atmosphere of dry nitrogen. The solvent is removed and residue is extracted in 10% methanol in CHCl₃ and saturated aqueous NaHCO₃. N-(3-ethynylphenyl)-6,7-bis(2-methoxyethoxy)quinazolin-4-amine base is separated chromatographically and converted to the hydrochloride salt in a solvent such as CHCl₃ using hydrochloric acid.

EP1044969 claims a method for preparing intermediates and compounds covering erlotinib. This patent discloses a process for preparing N-(3-ethynylphenyl)-6,7-bis(2-methoxyethoxy)quinazolin-4-amine which involves stirring 4-[3-[[6,7-bis(2-methoxyethoxy)-4-quinazolinyl]amino]phenyl]-2-methyl-3-butyn-2-ol with anhydrous sodium hydroxide and 2-methoxyethanol and heating at reflux for 47 hours. The reaction mixture is cooled to 20-25° C. and concentrated HCl is added to it. The resulting mixture is granulated at 20-25° C. to crystallize the product.

Indian patent application 902/CHE/2006 discloses a process for preparation of N-(3-ethynylphenyl)-6,7-bis(2-methoxyethoxy)quinazolin-4-amine hydrochloride. The process involves reacting 3,4-dihydroxy benzaldehyde with substituted ethylmethyl ether in the presence of an inert solvent and base to obtain 3,4-bis(2-methoxyethoxy) benzaldehyde. This 3,4-bis(2-methoxyethoxy) benzaldehyde is converted to 3,4-bis(2-methoxyethoxy) benzaldoxime in the presence of a base and organic solvent and is further dehydrated to 3,4-bis(2-methoxyethoxy) benzonitrile. The benzonitrile so obtained is nitrated to obtain 4,5-bis(2-methoxyethoxy)-2-nitrobenzonitrile which is further reduced to obtain 2-amino-4,5-bis(2-methoxyethoxy) benzonitrile. N'-(3-ethynylphenyl)-N,N-dimethyl formamidine obtained on formylation of 3-ethynylaniline with N,N-dimethyl formamidine is coupled with 2-amino-4,5-bis(2-methoxyethoxy) benzonitrile to obtain erlotinib free base which on treatment with a polar solvent containing hydrochloric acid gives erlotinib hydrochloride.

Indian patent application 904/CHE/2006 also discloses a process for preparation of N-(3-ethynylphenyl)-6,7-bis(2-methoxyethoxy)quinazolin-4-amine hydrochloride. The process involves reacting 3,4-dihydroxy benzaldehyde with substituted ethylmethyl ether in the presence of an inert solvent and base to obtain 3,4-bis(2-methoxyethoxy) benzaldehyde. This 3,4-bis(2-methoxyethoxy) benzaldehyde is converted to 3,4-bis(2-methoxyethoxy) benzaldoxime in the presence of a base and organic solvent and is further dehydrated to 3,4-bis(2-methoxyethoxy) benzonitrile. The benzonitrile so obtained is nitrated to obtain 4,5-bis(2-methoxyethoxy)-2-nitrobenzonitrile which is further reduced to get 2-amino-4,5-bis(2-methoxyethoxy) benzonitrile. 2-amino-4,5-bis(2-methoxyethoxy) benzonitrile is formylated with a formylating agent in the presence of formic acid derivative to obtain N'-[2-cyano-4,5-bis(2-methoxyethoxy)phenyl]-N,N-dimethylformamidine which is coupled with an aniline derivative to obtain erlotinib free base which on treatment with a polar solvent containing hydrochloric acid gives erlotinib hydrochloride.

The processes described in the prior art require anhydrous conditions and are carried out under an inert atmosphere. These processes are time consuming and cumbersome. Also a large variety of solvents are required for extraction and purification. Hence, there is a need for the development of a simple and industrially economical process.

OBJECT OF THE INVENTION

The object of the present invention is to provide an improved process for the synthesis of erlotinib and its pharmaceutically acceptable salts.

SUMMARY OF THE INVENTION

The present invention discloses an improved process for the synthesis of erlotinib and its pharmaceutically acceptable salts which process is simple and economical for commercial production.

According to a first aspect of the present invention, there is provided a process for the preparation of a salt of N-(3-ethynylphenyl)-6,7-bis(2-methoxyethoxy)quinazolin-4-amine comprising reacting a 4-halo-6,7-bis(2-methoxyethoxy) quinazoline with 3-aminophenyl acetylene or an acid salt thereof under acidic conditions to form the corresponding acid salt of N-(3-ethynylphenyl)-6,7-bis(2-methoxyethoxy) quinazolin-4-amine, the process optionally further comprising converting the acid salt of N-(3-ethynylphenyl)-6,7-bis (2-methoxyethoxy)quinazolin-4-amine to N-(3-ethynylphenyl)-6,7-bis(2-methoxyethoxy)quinazolin-4-amine.

In an embodiment, the acidic conditions are obtained by using an acid selected from the group consisting of a mineral acid, an organic acid or mixtures thereof. The acid may be selected from the group consisting of hydrochloric acid, hydrobromic acid, sulphuric acid, p-toluene sulphonic acid, benzoic acid, citric acid, succinic acid, oxalic acid, benzene sulphonic acid, tartaric acid, methane sulphonic acid, phosphoric acid and mixtures thereof. Preferably, the acid used is hydrochloric acid.

In an embodiment, the 4-halo-6,7-bis(2-methoxyethoxy) quinazoline is selected from 4-chloro-6,7-bis(2-methoxyethoxy) quinazoline, 4-bromo-6,7-bis(2-methoxyethoxy) quinazoline or 4-iodo-6,7-bis(2-methoxyethoxy) quinazoline. Preferably, the 4-halo-6,7-bis(2-methoxyethoxy) quinazoline is 4-chloro-6,7-bis(2-methoxyethoxy) quinazoline.

In an embodiment, the 3-aminophenyl acetylene is not in the form of a salt. In an alternative embodiment, the acid salt of 3-aminophenyl acetylene is the hydrochloride salt.

Typically, 4-chloro-6,7-bis(2-methoxyethoxy) quinazoline is reacted with 3-aminophenyl acetylene.

In an embodiment, the process is carried out in the presence of a solvent selected from the group consisting of water, $C_1$-$C_4$ alcohols, ketones, hydrocarbons or mixtures thereof. The solvent may be selected from the group consisting of water, dimethyl carbonate, special denatured spirit (SPDS), acetonitrile, acetone, isopropyl alcohol and mixtures thereof. The solvent may also be tetrahydrofuran, toluene or ethyl acetate. In an embodiment, the solvent is a mixture of solvents. For example, the mixture may be of acetonitrile and toluene, ethyl acetate and acetonitrile or acetone and water.

Following reaction of the 4-halo-6,7-bis(2-methoxyethoxy) quinazoline with the 3-aminophenyl acetylene or salt thereof, the acid salt of N-(3-ethynylphenyl)-6,7-bis(2-methoxyethoxy)quinazolin-4-amine may be converted to N-(3-ethynylphenyl)-6,7-bis(2-methoxyethoxy)quinazolin-4-amine. For example, the reaction mixture comprising the acid salt of N-(3-ethynylphenyl)-6,7-bis(2-methoxyethoxy) quinazolin-4-amine may be basified in the presence of a base to obtain N-(3-ethynylphenyl)-6,7-bis(2-methoxyethoxy) quinazolin-4-amine. The base may be selected from the group consisting of an organic base and an inorganic base. The base may be an alkali metal hydroxide or an alkali metal carbonate. In an embodiment, the base is selected from the group consisting of sodium hydroxide, potassium hydroxide, sodium carbonate, potassium carbonate, ammonia, pyridine and triethyl amine.

The process may be carried out a temperature below about 40° C. For example the process may be carried out a temperature ranging from about 20° C. to about 40° C., suitably from about 20° C. to about 35° C., preferably from about 25° C. to about 30° C.

In an embodiment, when the acid is added to the starting materials, the temperature may be from about 20° C. to about 35° C., preferably from 25° C. to 30° C. This temperature may be maintained during reaction or may be increased to around 35° C. to about 40° C.

The process may further comprise converting the N-(3-ethynylphenyl)-6,7-bis(2-methoxyethoxy)quinazolin-4-amine to a second salt. The salt may be the hydrochloride salt. Alternatively, the second salt may be the sulphate, oxalate, tosylate, phosphate, benzoate, citrate, succinate, benzene sulphonate, hydrobromide, tartrate or mesylate salt. The conversion may be carried out in any manner well known to the skilled person, for example by reacting the N-(3-ethynylphenyl)-6,7-bis(2-methoxyethoxy)quinazolin-4-amine with the corresponding acid. Thus, the sulphate, oxalate, tosylate, phosphate, benzoate, citrate, succinate, benzene sulphonate, hydrobromide, tartrate or mesylate salts may be prepared by reacting the N-(3-ethynylphenyl)-6,7-bis(2-methoxyethoxy) quinazolin-4-amine with sulphuric acid, oxalic acid, p-toluene sulphonic acid, phosphoric acid, benzoic acid, citric acid, succinic acid, benzene sulphonic acid, hydrobromic acid, tartaric acid or methane sulphonic acid, respectively.

In an embodiment, the N-(3-ethynylphenyl)-6,7-bis(2-methoxyethoxy)quinazolin-4-amine is converted to the hydrochloride salt using hydrochloric acid or hydrogen chloride gas in an organic solvent.

In an embodiment, the process is not carried out under an inert atmosphere. The process of the present invention may advantageously be carried out under atmospheric conditions. By "atmospheric conditions" is meant not under an inert atmosphere, at a temperature ranging from about 23° C. to about 27° C. and under atmospheric pressure.

According to another aspect of the present invention, there is provided erlotinib or a salt thereof prepared according to the process described above.

According to yet another aspect of the present invention, there is provided a pharmaceutical composition comprising erlotinib or a salt thereof prepared according to the process described above together with one or more pharmaceutically acceptable excipients. Suitable excipients are well known to those skilled in the art.

DETAILED DESCRIPTION

The first aspect of the present invention provides an improved process for preparation of N-(3-ethynylphenyl)-6,7-bis(2-methoxyethoxy)quinazolin-4-amine and its pharmaceutically acceptable salts. The process of the present invention is economical and commercially advantageous over the processes of the prior art.

Generally the reaction of the amine and chloro compound is carried out in the presence of a base which promotes the reaction to completion. However, surprisingly it has been found that the reaction of the present invention can be carried out in the presence of an acid which forms another aspect of the invention wherein N-(3-ethynylphenyl)-6,7-bis(2-methoxyethoxy)quinazolin-4-amine is prepared by reacting a 4-halo-6,7-bis(2-methoxyethoxy) quinazoline with 3-aminophenyl acetylene or an acid salt thereof under acidic conditions.

In one embodiment, the present invention provides a process which is carried out by reacting 4-chloro-6,7-bis(2-methoxyethoxy) quinazoline with 3-aminophenyl acetylene under acidic conditions.

Yet another aspect of the present invention provides the preparation of N-(3-ethynylphenyl)-6,7-bis(2-methoxyethoxy)quinazolin-4-amine by reacting a 4-halo-6,7-bis (2-methoxyethoxy) quinazoline with 3-aminophenyl acetylene or a salt thereof at a temperature below 40° C.

Further, the present invention provides preparation of N-(3-ethynylphenyl)-6,7-bis(2-methoxyethoxy)quinazolin-4-amine by reacting a 4-halo-6,7-bis(2-methoxyethoxy) quinazoline with 3-aminophenyl acetylene or a salt thereof in a suitable solvent.

In the process of the present invention, the acidic conditions may be obtained by using an acid selected from the group consisting of a mineral acid, an organic acid or mixtures thereof. The acid may be selected from the group consisting of hydrochloric acid, hydrobromic acid, sulphuric acid, p-toluene sulphonic acid, benzoic acid, citric acid, succinic acid, oxalic acid, benzene sulphonic acid, tartaric acid, methane sulphonic acid, phosphoric acid and mixtures thereof. Preferably the acid used is hydrochloric acid. The acid salt of erlotinib corresponds to the acidic conditions used, for example the use of hydrochloric acid will result in formation of the hydrochloride salt of erlotinib.

The acid salt of erlotinib may be isolated and not converted to erlotinib base, or may be converted to erlotinib base.

In an embodiment, the acid salt is purified before isolation, for example purified using a suitable solvent and dried. The solvent used for purification is preferably selected from $C_1$-$C_4$ alcohols, more preferably methanol.

In an alternate embodiment of the invention, the pharmaceutically acceptable salt of erlotinib is isolated. The salt may then be suspended in a suitable solvent and basified using a suitable base to obtain erlotinib. The base used may be selected from the group consisting of organic and inorganic bases. The base may be selected from the group consisting of sodium hydroxide, potassium hydroxide, sodium carbonate, potassium carbonate, ammonia, pyridine, triethyl amine. The so-obtained erlotinib may then be further converted to a second salt such as its hydrochloride salt, for example using hydrochloric acid or hydrogen chloride gas in a suitable organic solvent. Other second salts of erlotinib include the sulphate, oxalate, tosylate, phosphate, benzoate or mesylate salts.

One of the advantages of this reaction is that it does not require any heating as prior art processes require. For example, the process described in EP0817775 involves adding 3-ethynylaniline and 4-chloro-6,7-bis-(2-methoxyethoxy)quinazoline to isopropanol containing pyridine and refluxing the mixture. In an embodiment, the process of the present invention is carried out at a temperature below the reflux temperature of the solvent used.

Furthermore, the reaction proceeds faster under the conditions of the present invention. The acid catalyses the reaction and also aids in formation of the salt. The presence of an acid catalyst increases the rate of reaction and leads to completion of reaction without the formation of any major impurities.

The reaction is carried out in a suitable solvent which may be selected from the group consisting of water, $C_1$-$C_4$ alcohols, ketones, hydrocarbons or mixture thereof. The solvent used may be selected from the group consisting of water, dimethyl carbonate, special denatured spirit (SPDS), acetonitrile, acetone, isopropyl alcohol and mixtures thereof.

A further advantage is that the reaction may be carried out under atmospheric conditions and it does not require any inert reaction conditions as required in the process disclosed in EP0817775. The prior art reactions are complicated and very lengthy while the reaction of the present invention requires less time and is easy to carry out.

In an embodiment, the process of the present invention can be represented as shown in the following reaction scheme:

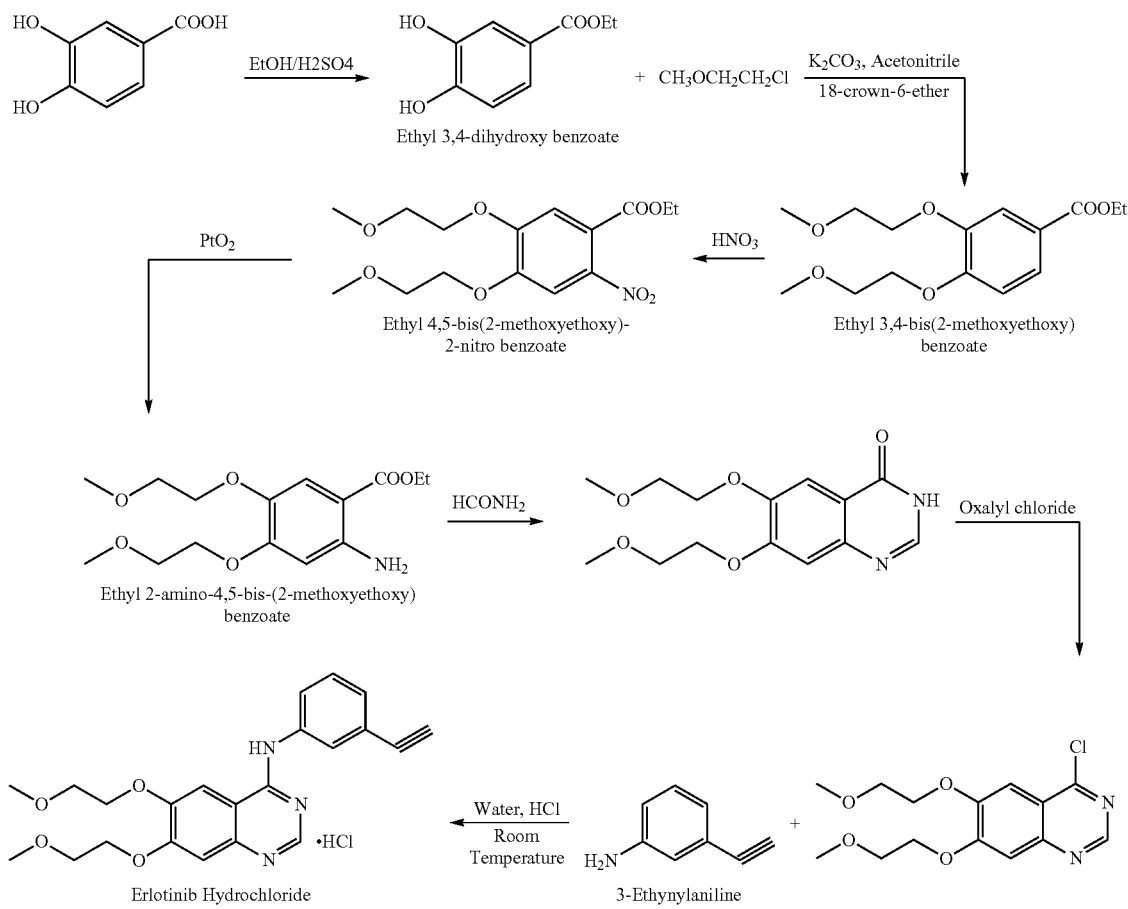

EXAMPLES

The present invention is now further illustrated by the following examples, which do not, in any way, limit the scope of the invention.

Example—1a

Preparation of Erlotinib Hydrochloride 5.0 g of 4-chloro-6,7-bis (2-methoxyethoxy) quinazoline was suspended in 75 ml water and 2.55 g of 3-aminophenyl acetylene was charged at 25-30° C. Further 1.0 ml 50% hydrochloric acid was added. The reaction mass was stirred at 25-30° C. for 2 hours. The solid obtained was filtered and washed with water. The product was dried at 40-45° C. to obtain 6.1 g of erlotinib hydrochloride.

In a similar manner, different solvents were used for preparing erlotinib hydrochloride under acidic conditions as given in table 1 below:

TABLE 1

| Example no. | Solvent used | Efficiency | HPLC Purity | Reaction Time |
|---|---|---|---|---|
| 1a | Water | 88.76% | 99.12% | 2 hours |
| 1b | Dimethyl carbonate | 77.50% | 98.50% | 1.5 hours |
| 1c | Denatured spirit | 87.31% | 99.03% | ½ hour |
| 1d | Acetonitrile | 91.67% | 97.44% | ½ hour |
| 1e | Isopropanol | 90.22% | 98.87% | ½ hour |
| 1f | Acetone | 90.22% | 98.40% | ½ hour |

Example—2a

Preparation of Erlotinib Hydrochloride 5.0 g of 4-chloro-6,7-bis(2-methoxyethoxy) quinazoline was suspended in 75 ml of water and 2.55 g of 3-aminophenyl acetylene was added at 25-30° C. followed by 1.0 ml of 50% hydrochloric acid. The reaction mass was heated at 35-40° C. for 1 hour. The solid obtained was filtered and washed with water. The product was dried at 40-45° C. to obtain 5.8 g of erlotinib hydrochloride.

In a similar manner, different solvents were used for preparing erlotinib hydrochloride under acidic conditions as given in table 2 below:

TABLE 2

| Example no. | Solvent used | Efficiency | HPLC Purity | Reaction time |
|---|---|---|---|---|
| 2a | Water | 85.40% | 99.22% | 1 hour |
| 2b | Denatured spirit | 96.04% | 99.25% | 1 hour |
| 2c | Tetrahydrofuran | 93.13% | 98.89% | 1 hour |
| 2d | Acetone | 87.31% | 98.81% | 1 hour |
| 2e | Acetonitrile | 96.33% | 99.23% | 1 hour |
| 2f | Acetonitrile + Toluene | 93.42% | 99.02% | 1 hour |
| 2g | Ethyl acetate + Acetonitrile | 96.04% | 83.74% | 1 hour |
| 2h | Acetone + water | 72.75% | 99.01% | 1 hour |

Example—3

Preparation of Erlotinib Hydrochloride 5 g of 4-chloro-6,7-bis(2-methoxyethoxy) quinazoline was suspended in 150 ml denatured spirit (SPDS) and 4.6 g of 3-aminophenyl acetylene was charged at 25-30° C. Further 1.0 ml of methane sulphonic acid was added. The reaction mass was stirred at 25-30° C. for 3 hours. Solid obtained was filtered, washed with SPDS and dried under vacuum. This solid was suspended in water, basified with ammonia and stirred for 10 minutes. The resulting erlotinib base was isolated, washed with water and dried under vacuum. The base was suspended in water and acidified to pH 1.0-2.0 using hydrochloric acid. The reaction mixture was stirred for 2 hours, filtered, washed with water and dried at 40-45° C. to obtain 5.8 g of erlotinib hydrochloride.

Example—4

Preparation of Erlotinib Hydrochloride 10.0 g of 4-chloro-6,7-bis(2-methoxyethoxy) quinazoline was suspended in 300 ml methanol and 9.2 g of 3-aminophenyl acetylene was charged at 25-30° C. Further 2.0 ml of benzoic acid was added. The reaction mass was stirred at 25-30° C. for 4 hours. Solid obtained was filtered, washed with methanol and dried under vacuum. This solid was suspended in water and then basified with sodium hydroxide and stirred for 10 minutes. The resulting erlotinib base was isolated, washed with water and dried under vacuum. The base was suspended in water and acidified to pH 1.0-2.0 using hydrochloric acid. The reaction mixture was stirred for 2 hours, filtered, washed with water and dried to obtain 11.2 g of erlotinib hydrochloride.

Example—5

Preparation of Erlotinib Hydrochloride 15.0 g of 4-chloro-6,7-bis(2-methoxyethoxy) quinazoline was suspended in 450 ml ethanol and 13.8 g of 3-aminophenyl acetylene was added at 25-30° C. Further 3.0 g tartaric acid was added. The reaction mass was stirred at 25-30° C. for 6 hours. Solid obtained was filtered, washed with water and dried under vacuum. This solid was suspended in water, basified with potassium hydroxide and stirred for 10 minutes. The resulting erlotinib base was isolated by filtration, washed with ethanol and dried under vacuum. The solid obtained was then suspended in water and acidified to pH 1.0-2.0 using hydrochloric acid. The reaction mixture was stirred for 2 hours, filtered, washed with water and dried at 40-45° C. to obtain 18.3 g of erlotinib hydrochloride.

Example—6

Preparation of Erlotinib Hydrochloride 50 g of 4-chloro-6,7-bis(2-methoxyethoxy) quinazoline was suspended in 1500 ml acetonitrile and 46 g of 3-aminophenyl acetylene was added at 25-30° C., followed by 10 ml acetic acid. The reaction mass was stirred at 25-30° C. for 30 minutes. Solid obtained was filtered, washed with water and dried under vacuum. This solid was suspended in water, basified with potassium hydroxide and stirred for 10 minutes. The resulting erlotinib base was isolated, washed with acetonitrile and dried under vacuum. The solid obtained was then suspended in water and acidified to pH 1.0-2.0 using hydrochloric acid. The reaction mixture was stirred for 2 hours, filtered, washed with water and dried at 40-45° C. to obtain 63 g of erlotinib hydrochloride.

Example 7

Preparation of Erlotinib Sulphate 1.98 Kg of 4-chloro-6,7-bis (2-methoxyethoxy) quinazoline was suspended in 30 litres of water and 1.0 Kg of 3-aminophenyl acetylene was charged at 25-30° C. Further 0.4 litres sulphuric acid was added. The reaction mass was heated and stirred at 35-40° C. for 1 hour. The solid obtained was filtered and washed with ethyl acetate. The product was dried at 38-40° C. to obtain 2.65 Kg of erlotinib sulphate.

Example 8

Preparation of Erlotinib Tosylate 5.0 g of 4-chloro-6,7-bis (2-methoxyethoxy) quinazoline was suspended in 75 ml ethyl acetate and 2.55 g of 3-aminophenyl acetylene was charged at 25-30° C. 0.9 g of p-toluyl sulphonic acid was added. The reaction mass was heated and stirred at 35-40° C. for 2 hours. The solid obtained was filtered and washed with ethyl acetate. The product was dried at 38-40° C. to obtain 6.6 g of erlotinib tosylate.

Example 9

Preparation of Erlotinib Oxalate 1.98 g of 4-chloro-6,7-bis (2-methoxyethoxy) quinazoline was suspended in 30 litres of acetone and 1.0 Kg of 3-aminophenyl acetylene was charged at 25-30° C. 0.7 Kg of oxalic acid was added. The reaction mass was heated and stirred at 35-40° C. for 2 hours. The solid obtained was filtered and washed with acetone. The product was dried at 38-40° C. to obtain 2.67 Kg of erlotinib oxalate.

Example 10

Preparation of Erlotinib Hydrochloride 1.98 Kg of 4-chloro-6,7-bis (2-methoxyethoxy) quinazoline was suspended in 30 litres of acetonitrile and 10 litres of toluene and 1.0 Kg of 3-aminophenyl acetylene was charged at 25-30° C. and hydrochloric acid was added. The reaction mass was heated and stirred at 35-40° C. for 6 hours. The solid obtained was filtered and washed with a mixture of acetonitrile and toluene. The product was dried at 38-40° C. to obtain 2.5 Kg of erlotinib hydrochloride.

It will be appreciated that the invention may be modified within the scope of the appended claims.

The invention claimed is:

1. A process for the preparation of an acid salt of N-(3-ethynylphenyl)-6,7-bis(2-methoxyethoxy)quinazolin-4-amine comprising reacting a 4-halo-6,7-bis(2-methoxyethoxy) quinazoline with 3-aminophenyl acetylene or an acid salt thereof under acidic conditions to form the corresponding acid salt of N-(3-ethynylphenyl)-6,7-bis(2-methoxyethoxy) quinazolin-4-amine, the process optionally further comprising converting the acid salt of N-(3-ethynylphenyl)-6,7-bis (2-methoxyethoxy)quinazolin-4-amine to N-(3-ethynylphenyl)-6,7-bis(2-methoxyethoxy)quinazolin-4-amine, wherein the process is carried out in the presence of a solvent selected from the group consisting of water, dimethyl carbonate, special denatured spirit (SPDS), acetonitrile, acetone, ethyl acetate, isopropyl alcohol and mixtures thereof, wherein the preparation of an acid salt of N-(3-ethynylphenyl)-6,7-bis(2-methoxyethoxy)quinazolin-4-amine is carried out at a temperature below 40° C.

2. The process according to claim 1, wherein the acidic conditions are obtained by using an acid selected from the group consisting of a mineral acid, an organic acid and mixtures thereof.

3. The process according to claim 2, wherein the acid is selected from the group consisting of hydrochloric acid, hydrobromic acid, sulphuric acid, p-toluene sulphonic acid, benzoic acid, citric acid, succinic acid, oxalic acid, benzene sulphonic acid, tartaric acid, methane sulphonic acid, phosphoric acid and mixtures thereof.

4. The process according to claim 3, wherein the acid used is hydrochloric acid.

5. The process according to claim 1, wherein the 4-halo-6,7-bis(2-methoxyethoxy) quinazoline is selected from 4-chloro-6,7-bis(2-methoxyethoxy) quinazoline, 4-bromo-6,7-bis(2-methoxyethoxy) quinazoline or 4-iodo-6,7-bis(2-methoxyethoxy) quinazoline.

6. The process according to claim 1, wherein the salt of 3-aminophenyl acetylene is a hydrochloride salt.

7. The process according to claim 1, wherein following reaction of the 4-halo-6,7-bis(2-methoxyethoxy) quinazoline with the 3-aminophenyl acetylene or salt thereof, the reaction mixture comprising the acid salt of N-(3-ethynylphenyl)-6,7-bis(2-methoxyethoxy)quinazolin-4-amine is basified in the presence of a base to obtain N-(3-ethynylphenyl)-6,7-bis(2-methoxyethoxy)quinazolin-4-amine.

8. The process according to claim 7, wherein the base is selected from the group consisting of organic and inorganic bases.

9. The process according to claim 7, wherein the base is selected from the group consisting of sodium hydroxide, potassium hydroxide, sodium carbonate, potassium carbonate, ammonia, pyridine and triethyl amine.

10. The process according to claim 1, wherein the acid salt of N-(3-ethynylphenyl)-6,7-bis(2-methoxyethoxy)quinazolin-4-amine is isolated and not converted to N-(3-ethynylphenyl)-6,7-bis(2-methoxyethoxy)quinazolin-4-amine.

11. The process according to claim 7, wherein the N-(3-ethynylphenyl)-6,7-bis(2-methoxyethoxy)quinazolin-4-amine is converted to a second salt.

12. The process according to claim 11, wherein the second salt is selected from the group consisting of hydrochloride, sulphate, oxalate, tosylate, phosphate, benzoate, citrate, succinate, benzene sulphonate, hydrobromide, tartrate and mesylate salt.

13. The process according to claim 12, wherein the second salt is hydrochloride salt.

14. The process according to claim 13, wherein the N-(3-ethynylphenyl)-6,7-bis(2-methoxyethoxy)quinazolin-4-amine is converted to the hydrochloride salt using hydrochloric acid or hydrogen chloride gas in an organic solvent.

15. The process according to claim 1, wherein the process is not carried out under an inert atmosphere.

16. The process according to claim 1, wherein the preparation of the acid salt of N-(3-ethynylphenyl)-6,7-bis(2-methoxyethoxy)quinazolin-4-amine has a reaction time less than 4 hours.

17. The process according to claim 16, wherein the preparation of the acid salt of N-(3-ethynylphenyl)-6,7-bis(2-methoxyethoxy)quinazolin-4-amine has a reaction time less than 3 hours.

18. The process according to claim 16, wherein the preparation of the acid salt of N-(3-ethynylphenyl)-6,7-bis(2-methoxyethoxy)quinazolin-4-amine has a reaction time of 0.5 hour or about 3 hours.

19. The process according to claim 16, wherein the preparation of the acid salt of N-(3-ethynylphenyl)-6,7-bis(2-methoxyethoxy)quinazolin-4-amine has a reaction time of about 2 hours to 3 hours.

* * * * *

UNITED STATES PATENT AND TRADEMARK OFFICE
CERTIFICATE OF CORRECTION

PATENT NO. : 8,642,758 B2  
APPLICATION NO. : 12/593212  
DATED : February 4, 2014  
INVENTOR(S) : Dharmaraj Ramachandra Rao and Rajendra Nanyanrao Kankan Page 1 of 1

It is certified that error appears in the above-identified patent and that said Letters Patent is hereby corrected as shown below:

In the Claims:

Column 10, Line 67, delete the word "about."
Column 11, Line 3, delete the word "about."

Signed and Sealed this
Fifteenth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,642,758 B2 Page 1 of 1
APPLICATION NO. : 12/593212
DATED : February 4, 2014
INVENTOR(S) : Rao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 487 days.

Signed and Sealed this
Twenty-ninth Day of September, 2015

Michelle K. Lee
*Director of the United States Patent and Trademark Office*